United States Patent [19]

Salmon et al.

[11] Patent Number: 5,707,354
[45] Date of Patent: Jan. 13, 1998

[54] COMPLIANT CATHETER LUMEN AND METHODS

[75] Inventors: Stephen Salmon, Sunnyvale; Ronald J. Jabba, Los Altos Hills, both of Calif.

[73] Assignee: Cardiovascular Imaging Systems, Inc., Sunnyvale, Calif.

[21] Appl. No.: 423,589

[22] Filed: Apr. 17, 1995

[51] Int. Cl.$^6$ ................................................. A61M 29/00
[52] U.S. Cl. ........................... 604/96; 604/99; 604/104; 604/93; 604/264; 604/280; 604/53; 128/658
[58] Field of Search ........................... 604/264, 280, 604/281, 282, 93, 96, 104, 97–100; 606/108; 128/662.06, 658

[56] References Cited

U.S. PATENT DOCUMENTS

| | | |
|---|---|---|
| 4,794,931 | 1/1989 | Yock . |
| 5,000,185 | 3/1991 | Yock . |
| 5,024,234 | 6/1991 | Leary et al. . |
| 5,117,831 | 6/1992 | Jang et al. . |
| 5,201,315 | 4/1993 | Griffith . |
| 5,203,338 | 4/1993 | Jang . |
| 5,211,627 | 5/1993 | William . |
| 5,219,335 | 6/1993 | Willard et al. . |
| 5,364,347 | 11/1994 | Jang . |
| 5,571,086 | 11/1996 | Kaplan et al. ........................... 604/96 |

*Primary Examiner*—Corrine M. McDermott
*Assistant Examiner*—Perry E. VanOver
*Attorney, Agent, or Firm*—Townsend and Townsend and Crew LLP

[57] ABSTRACT

In one aspect, the invention provides a vascular catheter sheath for use with a therapeutic catheter having a radially expandable member. The catheter sheath includes a catheter body having a proximal end, a distal end, and at least one lumen adapted to receive the therapeutic catheter. The catheter body further includes a compliant portion near the distal end, with the compliant portion being adaptable to conform to the shape of the expandable member when the expandable member is radially expanded in the lumen.

40 Claims, 3 Drawing Sheets

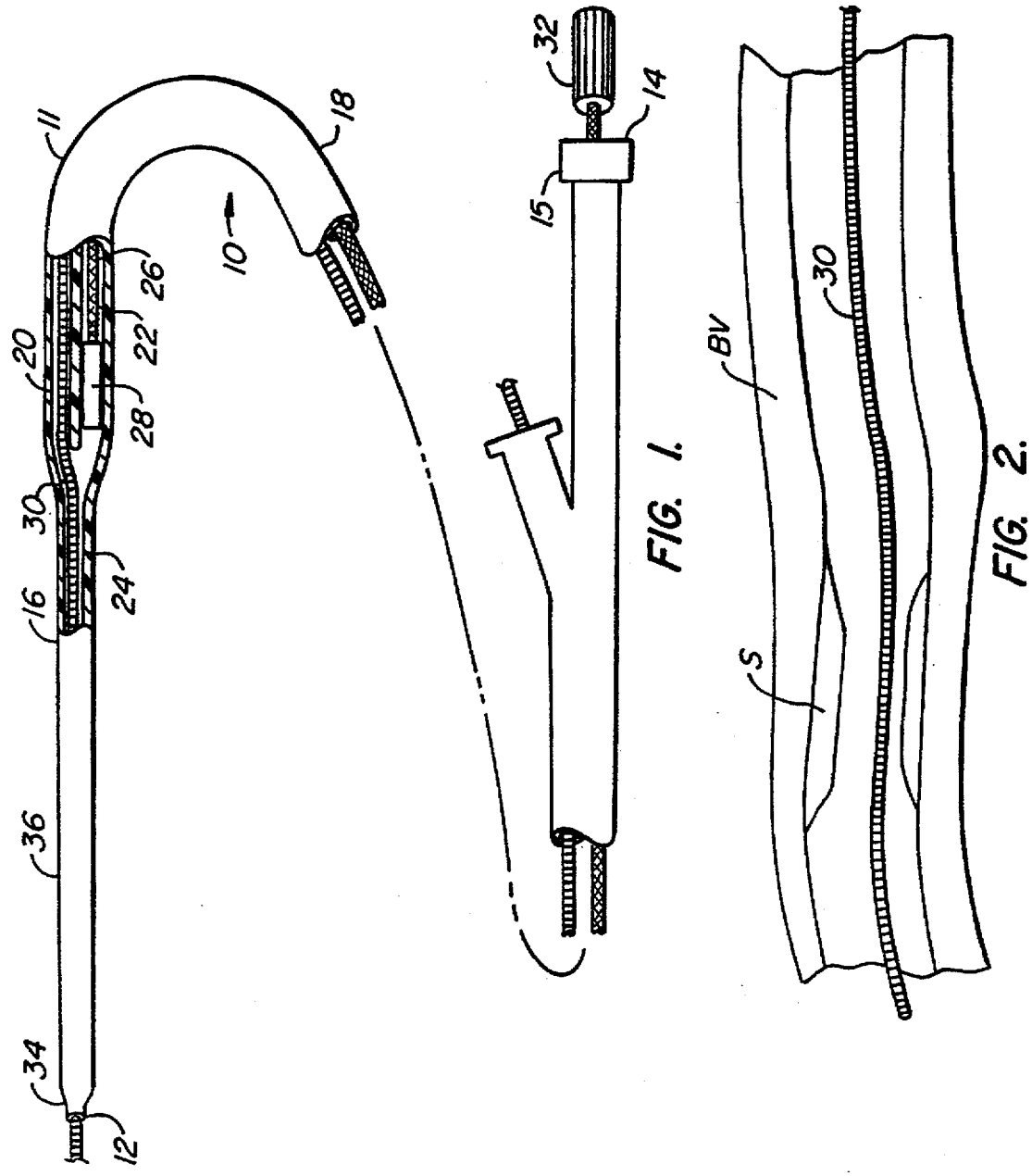

COMPLIANT CATHETER LUMEN AND METHODS

BACKGROUND OF THE INVENTION

1. Field of the Invention

The invention relates generally to the field of vascular catheters, and in particular to a vascular catheter sheath for receiving other diagnostic and/or therapeutic catheters or devices and having a compliant portion that can be radially expanded for therapeutic treatment of the vascular anatomy.

Arteriosclerosis, also known as atherosclerosis, is a common human ailment arising from the deposition of fatty-like substances, referred to as atheroma or plaque, on the walls of blood vessels. Such deposits occur both in the peripheral blood vessels that feed limbs of the body and coronary blood vessels that feed the heart. When deposits accumulate in localized regions of the blood vessels, blood flow is restricted and the person's health is at serious risk.

One well-accepted approach for diagnosing such vascular deposits is the use of intravascular ultrasonic imaging. Intravascular ultrasonic imaging usually employs mechanical rotation of an ultrasonic signal, either by mechanically rotating a transducer or by mechanically rotating a mirror, which radially deflects the ultrasonic signal from the transducer. Mechanical rotation generally requires rotating the transducer and/or associated mirror at speeds usually in the range from 500 to 2000 rpm. At such speeds, the interior blood vessel must be protected from the rotating components, which could cause substantial injury should they come in contact with the blood vessel.

A number of specific designs for mechanical ultrasonic imagers have been described. An early design is illustrated in U.S. Pat. No. 4,794,931, where the mechanical components of the imaging system are located within a housing at the distal end of the catheter. The housing includes a fixed guidewire at its distal tip which is used to position the catheter within the vascular system. Other designs use an "over-the-wire" configuration where the catheter may be introduced over a separate (movable) guidewire. The use of a movable guidewire offers certain advantages including improved steering capability through branch coronary arteries and elsewhere and easier catheter exchange, e.g., substitution of a therapeutic catheter after imaging has been completed. One such over-the-wire ultrasonic imaging catheter design is described in U.S. Pat. No. 5,024,234, disclosure of which is herein incorporated by reference.

Intravascular imaging catheters are intended to supply diagnostic information so that therapeutic procedures, such as angioplasty, atherectomy, laser ablation, stent deployment, and the like, can be performed on the stenotic region. For most of these procedures, once diagnosis by the imaging catheter has been performed, the imaging catheter is withdrawn from the stenotic region so that a therapeutic device can be introduced. Usually, the imaging catheter is inserted through an introducer sheath or guiding catheter. Once imaging has occurred and a catheter exchange is required, the imaging catheter is withdrawn from the sheath and is exchanged for the therapeutic catheter.

Of particular interest to the present invention are balloon angioplasty catheters having a balloon near its distal end for dilating the stenosed region. To perform a balloon angioplasty procedure using ultrasound, the vessel is first imaged with the imaging catheter. The imaging catheter will typically then be withdrawn from the introducer sheath or guiding catheter and exchanged for the angioplasty catheter. The angioplasty balloon catheter is then further advanced through the introducer sheath until the balloon passes beyond the distal end of the sheath and into the open vessel where it is aligned with the stenosed region. When the balloon is exposed to the stenosed region, the balloon is inflated to radially expand the vessel at the stenosed region. One particular drawback with such a treatment procedure is excessive vessel traumatization resulting from advancement and retraction of the balloon catheter within the vessel. Another drawback is that such a procedure usually requires the use of an elaborate angioplasty balloon catheter of the procedure. A further drawback is the time required to exchange catheters, thereby further increasing vessel trauma.

One proposed method for reducing catheter exchange time and resulting vessel trauma is to employ a "common lumen" catheter. Such a common lumen catheter design is described in U.S. Pat. No. 5,203,338, the disclosure of which is herein incorporated by reference. Briefly, the common lumen catheter has a proximal region having two or more lumens and a distal region having a common lumen that is connected to and is in communication with both of the lumens of the proximal region. The common lumen has a cross-sectional area which is less than the combined cross-sectional areas of the two lumens of the proximal region. Introduction of a common lumen catheter into a blood vessel is illustrated in copending U.S. patent application Ser. No. 08/183,458, filed Jan. 18, 1994, the disclosure of which is herein incorporated by reference. With the common lumen configuration, the proximal lumens can be used to hold a variety of therapeutic or diagnostic devices so that catheter exchange is reduced or eliminated. When a particular device is required, it can be advanced from one of the proximal lumens and into the common lumen.

Although common lumen-type catheters have been effective in reducing vessel trauma due to catheter exchange, a number of drawbacks still exist. For example, the common lumen catheter must still usually be withdrawn from the stenotic region in order for therapy to occur. This in turn increases the risk of vessel trauma during advancement of the catheter. Further, the distal end of the common lumen catheter must have a large enough dimension so that the therapeutic device can be passed therethrough, thereby reducing the trackability of the common lumen catheter and increasing the risk of vessel trauma. In the specific case of balloon angioplasty, retracting the deflated balloon into the common lumen could be difficult since balloon profile has increased after inflation.

It would therefore be desirable to provide a vascular catheter and methods whereby a vessel can be diagnosed and treated with reduced vessel trauma, reduced operating time, and reduced costs. In one particular aspect, the catheter and methods should allow for diagnosis and angioplasty therapy with minimal or no over-the-wire catheter exchanges. In another particular aspect, the vascular catheter and method should allow for both diagnosis and therapy, and particularly ultrasonic imaging diagnosis and angioplasty therapy, without having to directly expose the imaging or therapeutic device to the vessel. In a further aspect, the vascular catheter and methods should allow for the deployment of a stent under the guidance of ultrasound imaging.

2. Description of the Background Art

Use of intravascular ultrasound for imaging a vessel is described in U.S. Pat. Nos. 4,794,931 and 5,000,185.

A common lumen catheter design is described in U.S. Pat. No. 5,203,338, the disclosure of which was previously incorporated herein by reference.

U.S. Pat. Nos. 5,201,315; 5,211,627; and 5,219,335 describe catheter sheaths having two proximal lumens and a distal lumen.

An over-the-wire ultrasonic imaging catheter is described in U.S. Pat. No. 5,024,234, the disclosure of which was previously incorporated herein by reference.

U.S. Pat. No. 5,364,347 describes a catheter system having a balloon angioplasty device disposed about a common lumen.

SUMMARY OF THE INVENTION

In one aspect of the invention, a vascular catheter sheath is provided and is for use with a therapeutic catheter having a radially expandable member. The vascular catheter sheath includes a catheter body having a proximal end, a distal end, and at least one lumen adapted to receive the therapeutic catheter. The catheter body is provided with a compliant portion near its distal end, with the compliant portion being adaptable to conform to the shape of the expandable member when the expandable member is radially expanded in the lumen. In this way, the vascular catheter sheath need not be pulled back from the stenosed region of the vessel during therapy.

In a particularly preferable aspect, the compliant portion is integrally formed as part of the catheter body. Preferably, the compliant portion is radially expandable from within the lumen when subjected to a threshold pressure of at least 5 psi. Such a threshold pressure is sufficient to begin radially expanding the compliant portion from its original shape, and is usually low enough for most conventional balloon angioplasty catheters to overcome when inflated. In another aspect, the compliant portion has a length in the range from about 10 mm to about 200 mm. In still a further aspect, the compliant portion is constructed of a resilient material that conforms to the shape of the catheter body until radially expanded. In this way, trauma to the vessel is reduced when the vascular catheter sheath is inserted through the blood vessel. Preferably, the compliant portion has a diameter in the range from 0.5 mm to 2 mm when conforming to the shape of the catheter body and a diameter in the range from 1.5 mm to 5 mm when fully expanded, i.e. expanded to the same extent as the balloon on the balloon angioplasty catheter. In still a further aspect, the compliant portion is constructed of an elastomeric material, such as elastomeric polymers. In yet another aspect, the sheath is provided with a radially expandable stent that is disposed about the compliant portion. In this way, the stent can be radially expanded from within the sheath when expanding the expandable member.

In another aspect of the invention, an improved vascular catheter is provided. The vascular catheter is of the type having a catheter body with a proximal end and a distal end, with the catheter body including a proximal region having at least two lumens and a distal region having a common lumen connected to and in communication with both of the lumens in the proximal region. The common lumen has a cross-sectional area which is less than the combined cross-sectional areas of the two lumens of the proximal region. Such a vascular catheter is improved by providing a compliant portion in the distal region of the catheter body that can be radially expanded upon application of an internal pressure applied within the common lumen. Such a configuration reduces vessel trauma by allowing for reduced catheter exchange time and by allowing for therapy to occur within the common lumen. Catheter exchange time is reduced by allowing various catheters to occupy the proximal region at the same time. When one catheter is needed, it can be advanced into the common lumen. For example, an imaging catheter and a therapeutic catheter can both be held in the proximal region. When imaging is needed, the imaging catheter can be advanced into the common lumen. Once imaging has occurred, the imaging catheter can be pulled back into the proximal region and the therapeutic catheter is advanced to the common lumen. The therapeutic catheter can then be radially expanded to radially expand the compliant portion and to treat the stenosed region in the vessel while remaining in the vascular catheter. In this way, vessel trauma is reduced since therapy occurs within the vascular catheter.

In a particular preferable aspect, the distal end of the catheter body is tapered, with the distal end having an outer dimension that is smaller than an outer dimension of the distal region. Such a configuration allows for easier tracking of the vascular catheter through the vessel when introduced over a guidewire. The tapered distal end further serves to provide safety to the patient by preventing embolization of parts from the therapeutic catheter or imaging core in the unusual event that they break loose in the common lumen during use.

In one aspect, the compliant portion is integrally formed as part of the catheter body. Preferably, the compliant portion is radially expandable from within the common lumen when subjected to an internal pressure of at least 5 psi. In a further aspect, the compliant portion is constructed of an elastomeric material such as elastomeric polymers. In yet another aspect, the compliant portion has a length in the range from about 10 mm to 200 mm, and will usually conform to the length of the distal region. The compliant portion will preferably have a diameter in the range from 0.5 mm to 2.0 mm when conforming to the shape of the catheter body and a diameter in the range from 1.5 mm to 5.0 mm when radially expanded. In still another aspect, the catheter is provided with a radially expandable stent that is disposed about the compliant portion. Furthermore, the compliant portion is coated with an anti-clotting agent, such as heparin.

The invention provides a vascular catheter system having both a catheter sheath and a balloon angioplasty catheter. The catheter sheath has a catheter body with a proximal end, a distal end, and at least one lumen. The catheter body includes a compliant portion near the distal end that is radially expandable. The balloon angioplasty catheter has a proximal end, a distal end, and a balloon near the distal end. In this manner, the catheter can be passed through the lumen of the catheter sheath, and the balloon can be inflated to radially expand the compliant portion and to treat the vessel.

In one particular aspect, the catheter body includes a proximal region having at least two lumens and a distal region having a common lumen connected to and in communication with both of the lumens of the proximal region and having a cross-sectional area which is less than the combined cross-sectional areas of the two lumens of the proximal region. In another aspect, the distal end of the catheter body is tapered, with the distal end having an outer dimension that is smaller than an outer dimension of the distal region. In still a further aspect, the compliant portion is integrally formed as part of the catheter body. In yet another aspect, the vascular catheter system includes an ultrasonic imaging element for insertion into one of the lumens in the proximal region of the catheter sheath. In this way, imaging of the stenosed region can occur prior to inflation of the balloon. In still another aspect, the sheath is provided with a radially expandable stent that is disposed about the compliant portion. Furthermore, the compliant portion is coated with an anti-clotting agent, such as heparin.

The invention provides a method for treating a vascular body lumen. According to the method, a catheter sheath having a compliant portion near a distal end is introduced into the body lumen and positioned near an area of the lumen to be treated. A radially expandable member is then introduced through the catheter sheath and up to the compliant portion. The expandable member is then radially expanded within the compliant portion to radially expand the body lumen at the treatment area.

In a preferable aspect, the expandable member is a balloon which is inflated to radially expand the compliant portion and the body lumen. Before expansion of the radially expandable member, the catheter sheath is preferably introduced into the vessel over a guidewire. The guidewire can then be removed from the compliant portion before the expandable member is introduced and expanded. Alternatively, in the case where a very low profile balloon is employed, the balloon can be delivered over the guidewire while the guidewire is still in the vessel.

In still a further aspect, the treatment area is preferably ultrasonically imaged prior to introducing and positioning the radially expandable member in the compliant portion. In this way, an image of the stenotic region can be produced so that the expandable member can be aligned with the treatment area before expansion. Ultrasonic imaging preferably occurs by passing an ultrasonic imaging element through the catheter sheath and rotating the imaging element within the sheath. Once imaging and treatment have occurred, the expandable member is preferably constricted until the compliant portion substantially conforms to the shape of the distal region. At this point, the catheter sheath can be removed from the vascular system.

In another aspect of the method, the catheter sheath is further provided with a radially expandable stent that is disposed over the complaint portion. With such a configuration, the stent can be aligned with the treatment area and the balloon inflated to radially expand and place the stent at the treatment area. Preferably, the treatment area is ultrasonically imaged to obtain an image of the treatment area prior to positioning and expanding the stent.

The invention further provides a method for treating a vascular body lumen. According to the method, a catheter sheath having a compliant portion near a distal end and a radially expandable stent over the compliant portion is introduced into the body lumen. The stent is then positioned beyond an area of the lumen to be treated. The body lumen is then ultrasonically imaged to obtain an image of the treatment area. With the image, the catheter sheath is then retracted to align the stent with the treatment area. A radially expandable member is then introduced through the catheter sheath and up to the stent. With the stent properly aligned, the expandable member is radially expanded within the compliant portion to radially expand the stent within the body lumen at the treatment area.

BRIEF DESCRIPTION OF THE DRAWINGS

FIG. 1 illustrate an exemplary embodiment of a vascular catheter sheath having a compliant portion near its distal end according to the present invention.

FIGS. 2–5 illustrate an exemplary method for treating a stenosed region of a blood vessel using the vascular catheter sheath of FIG. 1.

DETAILED DESCRIPTION OF THE SPECIFIC EMBODIMENTS

Figure 3:
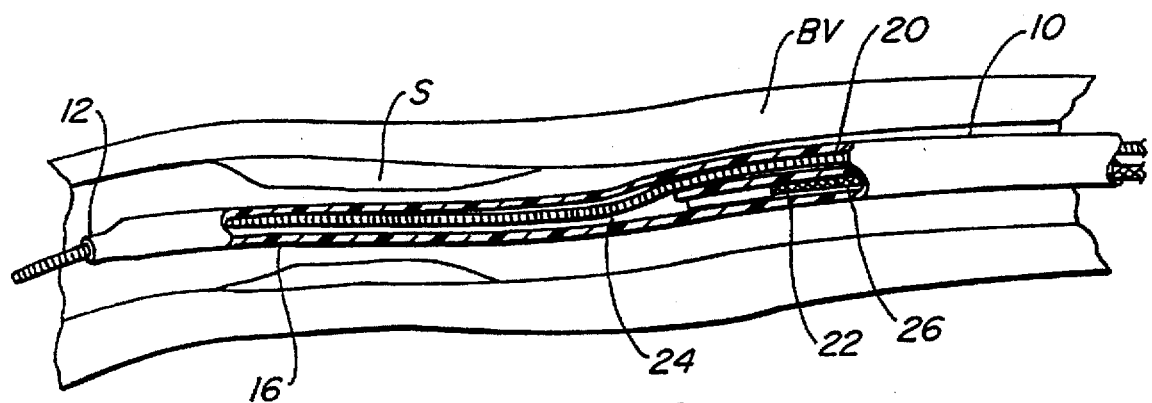
Figure 4:
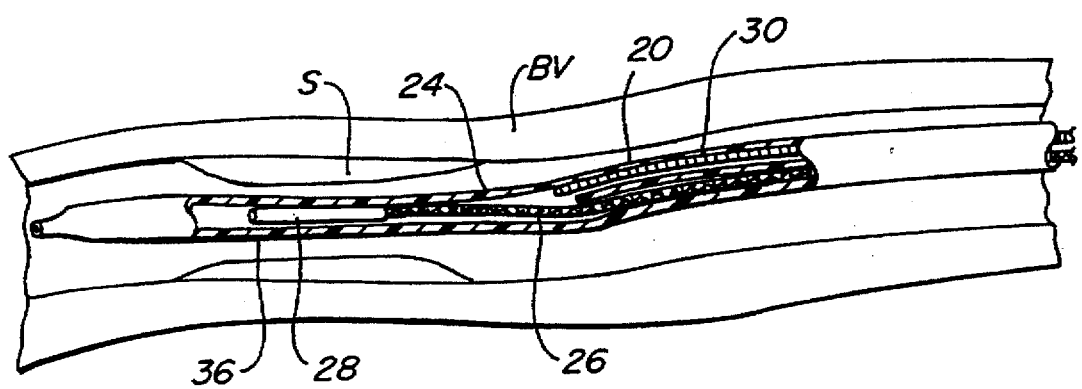

The invention provides a vascular catheter sheath and methods for therapeutically treating a blood vessel. The catheter sheath and methods can be used for providing a variety of therapeutic treatments, but will find its greatest use in angioplasty procedures. The vascular catheter sheath of the invention includes a catheter body having a proximal end, a distal end, and at least one lumen. The vascular catheter sheath is preferably for use with a therapeutic catheter having a radially expandable member, preferably a balloon. The catheter body of the catheter sheath includes a portion near its distal end (and sometimes even the entire sheath) that can radially expand when subjected to an internal pressure. In this way, radial expansion of the therapeutic catheter within the lumen of the catheter sheath radially expands the catheter body which in turn radially expands the blood vessel to provide therapy. The portion of the catheter sheath that is radially expandable is preferably constructed of a compliant material. As used herein, the term "compliant" means that the walls of the catheter body are able to conform or adhere to the shape of the expandable element when the expandable element is radially expanded. In this way, a compliant portion is provided near the distal end of the vascular catheter sheath that is both radially expandable and is compliant to the shape of the expandable element when radially expanded to treat the stenosed region of the vessel. Further, the compliant portion can also be constructed of a resilient material, i.e., one that will return to its original shape after expansion. In this manner, the compliant portion can be integrally formed as part of the catheter body and with a shape that conforms to the shape of the catheter body until expanded by the expandable member of the therapeutic catheter. After therapy has occurred and the expandable member is compressed, the resiliency of the compliant portion allows it to return to its original shape conforming to the shape of the catheter sheath.

The compliant portion is preferably constructed of a material having the requisite properties for compliance and meeting traditional catheter performance requirements, such as trackability. The compliant portion will preferably be constructed of a material having plastic properties, and more specifically, having mechanical properties similar to (but not necessarily identical to) a thermoplastic elastomer. Such elastomers are plastic materials that can be stretched repeatedly and upon immediate release of the stress return to their original physical dimension. A further requirement for the compliant portion is that it should be biocompatible with the patient's anatomy and have good acoustic transmission characteristics.

Elastomers are a preferred material because of their viscoelastic properties. When stretched below the proportional limit, the elastomers exhibit a linear stress-strain relationship as dictated by Hooke's Law where stress is proportional to the strain. When below the proportional limit, the behavior of the plastic material is elastic in nature allowing for deformations to be recoverable when a stress is released. In this way, the compliant portion can conform to the shape of the catheter body until radially expanded by the therapeutic catheter. When the expandable member on the therapeutic catheter is constricted, the compliant portion recovers to its original shape conforming to the shape of the catheter body.

The material used to construct the compliant portion should also have minimal creep. When stress is applied to an elastomer, the elastic deformation begins and continues until the load is removed. Once the load is removed, the elastomer usually exhibits an elastic recovery. Sometimes, however, the material does not fully recover; i.e., experiences a permanent set. Permanent set of the compliant portion should be kept minimal.

An advantage of thermoplastic elastomers and rubbers is that they are melt processable and therefore can be formed into the required configuration. Further, many of these materials can be copolymerized or blended to achieve the required physical properties as previously described. For example, melt processable rubber such as styrene-butadiene-styrene, styrene-isoprene-styrene, or styrene-ethylene/butylene-styrene can be used to manufacture extruded tubing. Blending such materials with polyolefins improves bondability to catheter shafts.

Solution or dip coating of elastomeric materials can also be employed to provide the required configuration of the compliant portion. Materials such as latex or Tactylon™ can be manufactured into tubing and still possess elastic properties similar to rubber compounds. Polyester urethanes as well as fluorosilicone polymers have suitable immediate elastic recovery and permanent set physical properties suitable for construction of the compliant portion.

Other alternative materials for construction of the compliant portion include Kraton G, a styrene-ethylene/butylene-styrene (SEBS) triblock copolymer in conjunction with standard commercially available percutaneous transluminal coronary angioplasty (PTCA) catheters ranging in size from 2 to 4 mm in diameter.

The compliant portion is preferably radially expandable when the interior walls of the catheter body are subjected to a threshold pressure of at least 5 psi. At such a threshold pressure, the walls begin to radially expand. Usually, the pressure required to further expand the catheter body increases above the threshold amount. Preferably, the pressure to fully expand the complaint portion to match to the radial expansion of the balloon on the balloon angioplasty catheter is well within the pressures required to fully inflate most conventional balloon angioplasty catheters. In this way, the walls of the compliant portion can be radially expanded for therapy by inflating the balloon angioplasty catheter using normal pressure ranges. The compliant portion will preferably have a length that is equal to or greater than the length of the expandable member of the therapeutic catheter. Preferably, the compliant portion will have a length in the range from about 10 mm to 200 mm. As previously described, the compliant portion will preferably conform to the shape of the catheter body until radially expanded. Preferably, the compliant portion will have a diameter in the range from about 0.5 mm to about 2.0 mm when conforming to the shape of the catheter body and a diameter in the range from 1.5 mm to 5.0 mm when radially expanded.

The therapeutic catheter employed to radially expand the compliant portion will usually be a balloon angioplasty catheter having a balloon near its distal end. An incompressible fluid is delivered to the balloon to inflate the balloon and to radially expand the compliant portion. A variety of such catheters are well known and commercially available, and include both fixed tipped and over-the-wire designs. Alternatively, less sophisticated and less costly designs can be provided since the balloon remains in and is protected by the sheath at all times during therapy.

The vascular catheter sheath of the invention can be provided with a single axial lumen or can alternatively be provided with a variety of lumens, a requirement being that the expandable member of the therapeutic catheter is able to be introduced through the catheter sheath and up to the compliant portion. As described in greater detail hereinafter with reference to FIG. 1, an exemplary vascular catheter sheath is the common lumen-type catheter sheath having a distal region and a proximal region. The distal region has a common lumen that is connected to and in communication with at least two lumens in the proximal region. The distal region further has a cross-sectional area which is less than the combined cross-sectional areas of the two lumens of the proximal region. The compliant portion is provided in the common lumen section. In this manner, a variety of diagnostic or therapeutic catheters or other devices, including guidewires, can be used with the same catheter sheath while sharing use of the common lumen.

Referring now to FIG. 1, an exemplary embodiment of a vascular catheter sheath 10 will be described. The catheter sheath 10 includes a catheter body 11 having a distal end 12 and a proximal end 14. The catheter sheath 10 further includes a distal region 16 and a proximal region 18. The proximal region 18 is provided with a pair of lumens 20, 22 that are connected to and in communication with a common lumen 24 in the distal portion 16. The proximal lumens 20, 22 are provided for holding a variety of diagnostic and/or therapeutic devices or catheters and which in turn can be advanced into the common lumen 24. Held in proximal lumen 22 is an ultrasonic imaging core 26 having an ultrasonic imaging element 28. Held in the proximal lumen 20 and extending into the common lumen 24 is a guidewire 30. As described in greater detail hereinafter, the catheter sheath 10 can be introduced into the vascular anatomy over the guidewire 30 by passing the guidewire 30 through the common lumen and into the proximal lumen 20. After insertion, the guidewire 30 can be withdrawn from the common lumen 24 and the ultrasonic imaging core 26 can be introduced into the distal portion 16. The ultrasonic imaging core 26 includes a connector 32 so that the imaging core 26 can be rapidly rotated to produce an image of the interior walls of the vessel. At the proximal end 14 is an o-ring 15 for providing a seal around the imaging core 26.

The distal end 12 of the catheter sheath 10 includes a taper 34 that reduces the distal profile of the catheter sheath 10. The distal end 12 is tapered such that the common lumen 24 at the distal end 12 is sized just large enough to allow the guidewire 30 to pass therethrough. Tapering of the distal end 12 in this manner is advantageous in that trackability of the catheter sheath 10 is improved when introduced into the vascular anatomy. Further, reduction in size of the distal end 12 provides a safety net to catch particulate in the unlikely event of balloon catheter or imaging element failure.

Integrally formed as part of the catheter body 11 is a compliant portion 36. The compliant portion is formed as part of the walls of the common lumen 24. In this way, when a therapeutic device is introduced into the common lumen and is radially expanded, the compliant portion 36 complies to the shape of the therapeutic device and is in turn radially expanded within the vessel. Although any portion of the distal region 16 can be made to have compliant properties, the entire distal region 16 will preferably be radially expandable.

Referring to FIGS. 2–5, an exemplary method for treating a stenosed region S of a blood vessel BV using the catheter sheath 10 of FIG. 1 will be described. Initially, the guidewire 30 is introduced into the blood vessel BV as is known in the art. As shown in FIG. 3, the catheter sheath 10 is then introduced over the guidewire 30 by passing the guidewire 30 through the distal end 12, through the common lumen 24, and into the proximal lumen 20. The catheter sheath 10 is advanced over the guidewire 30 until the distal region 16 is at or near the stenosed region S. At this point, the guidewire is retracted from the common lumen and the ultrasonic imaging core 26 is advanced through the proximal lumen 22 so that an image of the blood vessel BV can be provided.

The imaging element 28 is rotated near or at the stenosed region S to produce an image of the stenosed region S. The resulting image allows the compliant portion 36 to be aligned with the stenosed region S, if needed. More importantly, the image allows for the balloon on the therapeutic catheter to be aligned with the stenosed region S when inserted into the compliant portion 36. Optionally, the compliant portion 36 can be provided with an ultrasonically opaque marker to help locate the compliant portion 36 relative to the stenosed region S and to help align the balloon with the stenosed region S.

One advantage of the catheter sheath 10 is that the stenosed region S can be visualized ultrasonically from within the common lumen 24. In this way, once imaging has occurred, the ultrasonic imaging core 26 can be withdrawn from the common lumen 24 and a therapeutic catheter introduced therein while the catheter sheath 10 remains stationary. This reduces both catheter exchange time and vessel trauma.

Figure 5:
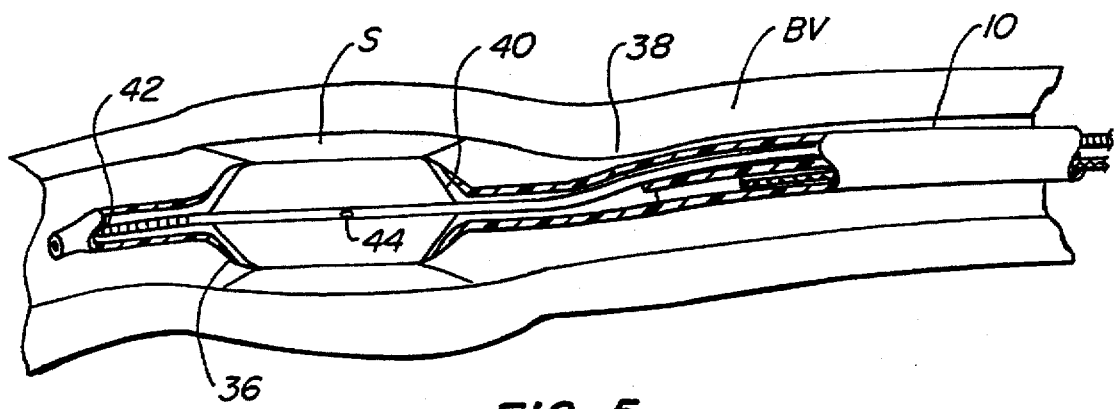

Referring to FIG. 5, the therapeutic catheter is illustrated as an angioplasty balloon catheter 38 having a balloon 40 near a distal end 42. The balloon 40 is inflated via an inflation port 44 that in turn is connected to a central lumen running through the balloon catheter 38. As the balloon 40 is inflated, it radially expands to engage the walls of the catheter body 11 at the compliant portion 36. The compliant portion 36 complies or adheres to the shape of the balloon 40 and hence radially expands along with the balloon 40. The balloon 40 is inflated until the compliant portion 36 engages the stenosed region S. The balloon 40 is then further inflated to complete the angioplasty procedure in a conventional manner known in the art.

By providing the common lumen 24, trauma to the blood vessel BV is lessened because exchange of the ultrasonic imaging catheter 26 and the angioplasty balloon catheter 38 occur within the catheter sheath 10, thereby reducing exchange time. Vessel trauma is further reduced because the need to pull back the sheath 10 to gain access to the stenosed region S after imaging is eliminated. Further, the invention eliminates the need to advance the balloon 40 beyond the distal end 12 to expose the balloon 40 to the stenosed region S, thereby reducing further trauma to the vessel.

The invention can employ a variety of angioplasty balloon catheters, including those well-known in the art. For example, the angioplasty balloon catheter 38 is a fixed tip type catheter having a guidewire tip 46 at the distal end 42. The guidewire tip 46 assists in tracking the balloon catheter 38 through the proximal lumen 20 and eliminates the need for a separate guidewire for introduction. Optionally, the balloon catheter 38 can itself be a guidewire, thereby eliminating the need for the guidewire 30. In this manner, the balloon catheter 38 can serve as the guidewire to insert the catheter sheath 10 as well as for providing therapeutic treatment to the stenosed region S when within the sheath 10. In another alternative, the balloon catheter can be an over-the-wire type that is inserted over a guidewire. Such a catheter can be advanced through the catheter sheath 10 over the guidewire 30. In this manner, proximal lumen 20 can be used to track over the guidewire 30 when the sheath 10 is inserted into the vessel BV and also to receive the over-the-wire balloon catheter.

Other balloon catheter designs can also be developed with less sophisticated features since the balloon catheter is protected by the sheath 10 at all times during therapy. Further, the catheter sheath 10 can be provided with more than two proximal lumens so that the sheath 10 can simultaneously hold the guidewire 30, the imaging core 26, and the balloon catheter 38.

In one particular aspect, the catheter sheath of the invention can be used to assist in placing a radially expandable stent within the blood vessel. The stent is placed over the compliant portion in a manner similar to the placement of conventional stents, such as those commercially available from Johnson & Johnson and Cook, which employ balloon delivery catheters. In this way, the stent can be radially expanded within the blood vessel by introducing a balloon into the compliant portion of the sheath and by inflating the balloon. Preferably, ultrasonic imaging is employed to assist in the alignment of the stent with the treatment area before the stent is deployed.

Figure 6:
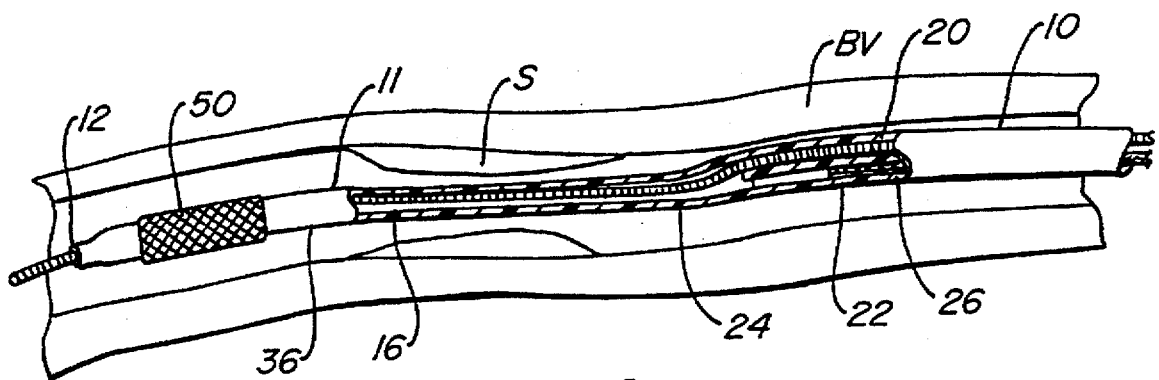
FIGS. 6–8 describe an alternative method for treating a stenosed region of a blood vessel with a stent using the vascular catheter sheath of FIG. 1.
Figure 7:
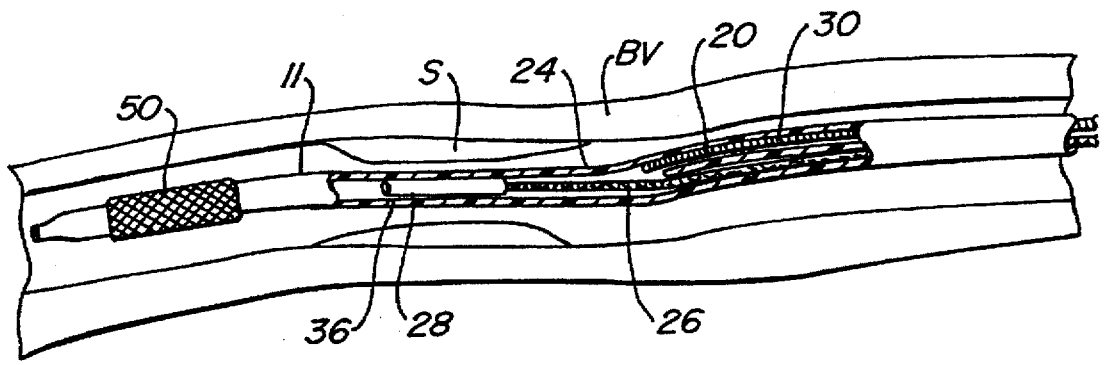
Figure 8:
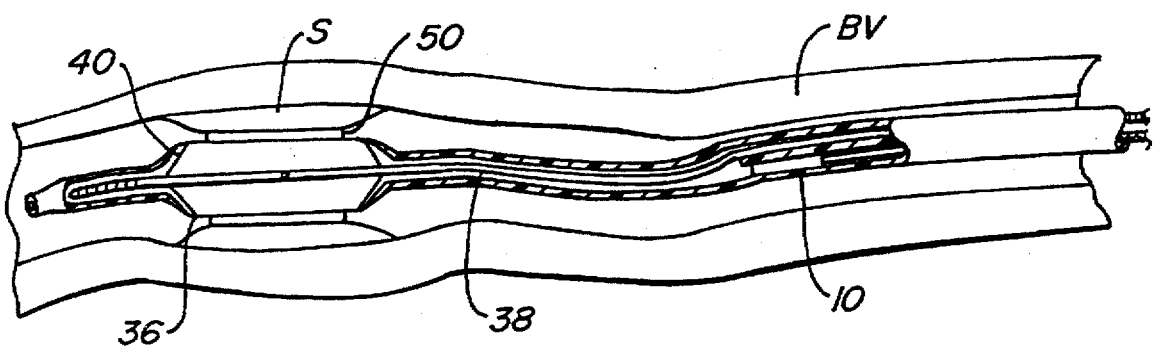

Referring to FIGS. 6–8, and exemplary method for introducing a stent 50 over the catheter sheath 10 of FIG. 1 will be described. The stent 50 is disposed about the periphery of the compliant portion 36, usually by crimping the stent 50 about the catheter body 11. With the stent 50 disposed about the compliant portion 36, the catheter sheath 10 is introduced into the blood vessel BV over the guidewire 30 as shown in FIG. 6. The sheath 10 is advanced to a position near the distal end of the guidewire 30 so that the stent 50 is distally beyond the stenosed region S. The guidewire 50 is then pulled back into the proximal lumen 20 as shown in FIG. 7, and the ultrasonic imaging core 26 is advanced into the common lumen 24. Imaging then occurs to locate the stenosed region S as previously described. After imaging, the imaging catheter 26 is withdrawn into the proximal lumen 22, and the catheter sheath 10 is pulled back within the blood vessel BV until the stent 50 is aligned with the stenosed region S as shown in FIG. 8. The balloon catheter 38 is then introduced into the common lumen 24 in the manner previously described and the balloon 40 is inflated to radially expand both the compliant portion 36 and the stent 50. After deployment of the stent 50, the balloon 40 is deflated and the catheter sheath 10 is withdrawn from the blood vessel BV leaving the stent 50 in place.

Although the foregoing invention has described in some detail by way of illustration and example, for purposes of clarity of understanding, it will be obvious that certain changes and modifications may be practiced within the scope of the appended claims.

What is claimed is:

1. A vascular catheter sheath for use with a therapeutic catheter having a radially expandable member, said vascular catheter sheath comprising:

a catheter body having a proximal end, a distal end, and at least one lumen adapted to receive the therapeutic catheter, wherein the catheter body includes a compliant portion near the distal end, said complaint portion being adaptable to conform to the shape of the expandable member when the expandable member is radially expanded in the lumen wherein the compliant portion is radially expandable from within the lumen when subjected to a threshold pressure of at least 5 psi.

2. The vascular catheter of claim 1, wherein the compliant portion is integrally formed as part of the catheter body.

3. The vascular catheter of claim 1, wherein the compliant portion has a length in the range from about 10 mm to 200 mm.

4. The vascular catheter of claim 1, wherein the compliant portion is constructed of a resilient material that conforms to the shape of the catheter body until radially expanded.

5. The vascular catheter of claim 4, wherein the compliant portion has a diameter in the range from 0.5 mm to 2.0 mm when conforming to the shape of the catheter body and a diameter in the range from 1.5 mm to 5.0 mm when radially expanded.

6. The vascular catheter of claim 1, wherein the compliant portion is constructed of an elastomeric polymer.

7. The vascular catheter of claim 1, further comprising a radially expandable stent disposed around the compliant portion.

8. An improved vascular catheter of the type having a catheter body with a proximal end and a distal end, wherein the catheter body includes a proximal region having at least two lumens and a distal region having a common lumen connected to and in communication with both of the lumens of the proximal region and having a cross-sectional area which is less than the combined cross-sectional areas of the two lumens of the proximal region, wherein the improvement comprises a compliant portion in the distal region of the catheter body that can be radially expanded upon application of an internal pressure applied within the common lumen, and wherein the complaint portion is radially expandable from within the common lumen when being subjected to an internal threshold pressure of at least 5 psi.

9. The vascular catheter of claim 8, wherein the distal end of the catheter body is tapered, with the distal end having an outer dimension that is smaller than an outer dimension of the distal region.

10. The vascular catheter as in claim 8, wherein the compliant portion is integrally formed as part of the catheter body.

11. The vascular catheter of claim 10, wherein the compliant portion has a diameter in the range from 0.5 mm to 2.0 mm when conforming to the shape of the catheter body and a diameter in the range from 1.5 mm to 5.0 mm when radially expanded.

12. The vascular catheter of claim 8, wherein the compliant portion is constructed of an elastomeric polymer.

13. The vascular catheter of claim 8, wherein the compliant portion has a length in the range from about 10 mm to 200 mm.

14. The vascular catheter of claim 8, wherein the distal region has a length in the range from about 10 mm to 200 mm.

15. The vascular catheter of claim 8, further comprising a radially expandable stent disposed around the compliant portion.

16. A vascular catheter system comprising:
   a catheter sheath having a catheter body with a proximal end, a distal end and at least one lumen, wherein the catheter body includes a compliant portion near the distal end that is radially expandable; and
   a balloon angioplasty catheter having a proximal end, a distal end, and a balloon near the distal end, wherein the catheter can be passed through the lumen of the catheter sheath, and wherein the balloon can be expanded to radially expand the compliant portion.

17. The vascular catheter system of claim 16, wherein the catheter body further includes a proximal region having at least two lumens and a distal region having a common lumen connected to and in communication with both of the lumens of the proximal region and having a cross-sectional area which is less than the combined cross-sectional areas of the two lumens of the proximal region.

18. The vascular catheter system of claim 17, wherein the distal end of the catheter body is tapered, with the distal end having an outer dimension that is smaller than an outer dimension of the distal region.

19. The vascular catheter system of claim 16, wherein the compliant portion is integrally formed as part of the catheter body.

20. The vascular catheter system of claim 16, further comprising an ultrasonic imaging element for insertion into the lumen of the catheter sheath.

21. The vascular catheter system of claim 16, further comprising a radially expandable stent disposed around the compliant portion.

22. A vascular catheter sheath for use with a therapeutic catheter having a radially expandable member, said vascular catheter sheath comprising:
   a catheter body having a proximal end, a distal end, and at least one lumen adapted to receive the therapeutic catheter, wherein the catheter body includes a compliant portion near the distal end, said complaint portion being adaptable to conform to the shape of the expandable member when the expandable member is radially expanded in the lumen, wherein the compliant portion is constructed of a resilient material that conforms to the shape of the catheter body until radially expanded, and wherein the compliant portion has a diameter in the range from 0.5 mm to 2.0 mm when conforming to the shape of the catheter body and a diameter in the range from 1.5 mm to 5.0 mm when radially expanded.

23. The vascular catheter of claim 22, wherein the compliant portion is radially expandable from within the lumen when subjected to a threshold pressure of at least 5 psi.

24. A vascular catheter sheath for use with a therapeutic catheter having a radially expandable member, said vascular catheter sheath comprising:
   a catheter body having a proximal end, a distal end, and at least one lumen adapted to receive the therapeutic catheter, wherein the catheter body includes a compliant portion near the distal end, said complaint portion being adaptable to conform to the shape of the expandable member when the expandable member is radially expanded in the lumen, and wherein a radially expandable stent is disposed around the compliant portion.

25. An improved vascular catheter of the type having a catheter body with a proximal end and a distal end, wherein the catheter body includes a proximal region having at least two lumens and a distal region having a common lumen connected to and in communication with both of the lumens of the proximal region and having a cross-sectional area which is less than the combined cross-sectional areas of the two lumens of the proximal region, wherein the improvement comprises a compliant portion in the distal region of the catheter body that can be radially expanded upon application of an internal pressure applied within the common lumen, and wherein the distal end of the catheter body is tapered, with the distal end having an outer dimension that is smaller than an outer dimension of the distal region.

26. The vascular catheter of claim 25, wherein the complaint portion is radially expandable from within the common lumen when being subjected to an internal threshold pressure of at least 5 psi.

27. An improved vascular catheter of the type having a catheter body with a proximal end and a distal end, wherein the catheter body includes a proximal region having at least two lumens and a distal region having a common lumen connected to and in communication with both of the lumens of the proximal region and having a cross-sectional area which is less than the combined cross-sectional areas of the two lumens of the proximal region, wherein the improvement comprises a compliant portion in the distal region of the catheter body that can be radially expanded upon application of an internal pressure applied within the common lumen, wherein the distal region has a length in the range from about 10 mm to 200 mm, and wherein the compliant portion has a diameter in the range from 0.5 mm to 2.0 mm when conforming to the shape of the catheter body and a diameter in the range from 1.5 mm to 5.0 mm when radially expanded.

28. An improved vascular catheter of the type having a catheter body with a proximal end and a distal end, wherein the catheter body includes a proximal region having at least two lumens and a distal region having a common lumen connected to and in communication with both of the lumens of the proximal region and having a cross-sectional area which is less than the combined cross-sectional areas of the two lumens of the proximal region, wherein the improvement comprises a compliant portion in the distal region of the catheter body that can be radially expanded upon application of an internal pressure applied within the common lumen, and wherein a radially expandable stent is disposed around the compliant portion.

29. A method for treating a vascular body lumen, comprising:

introducing a catheter sheath having a distal end and a compliant portion near the distal end into the body lumen and positioning the compliant portion near an area of the lumen to be treated;

introducing a radially expandable member through the catheter sheath and up to the compliant portion; and radially expanding the expandable member within the compliant portion to radially expand the body lumen at the treatment area.

30. The method of claim 29, further comprising introducing the catheter sheath over a guidewire.

31. The method of claim 30, further comprising removing the guidewire from the compliant portion before introducing the expandable member.

32. The method of claim 30, further comprising advancing the expandable member over the guidewire.

33. The method of claim 29, further comprising ultrasonically imaging the treatment area to obtain an image of the treatment area prior to expanding the expandable member.

34. The method of claim 33, wherein the treatment area is ultrasonically imaged by passing an ultrasonic imaging element through the catheter sheath and rotating the imaging element.

35. The method of claim 34, further comprising maintaining the compliant portion in substantially the same position in the body lumen while both ultrasonically imaging the vessel and radially expanding the expandable member.

36. The method of claim 29, wherein the catheter sheath includes a distal region which is distal to the compliant portion, and further comprising constricting the expandable member until the compliant portion substantially conforms to the shape of the distal region and removing the catheter sheath from the body lumen.

37. The method of claim 29, wherein the expandable member is a balloon, and further comprising inflating the balloon to radially expand the body lumen.

38. The method of claim 37, wherein the catheter sheath further includes a radially expandable stent disposed over the compliant portion, and wherein the method further comprises aligning the stent with the treatment area and inflating the balloon to radially expand the stent at the treatment area.

39. The method of claim 38, further comprising ultrasonically imaging the treatment area to obtain an image of the treatment area prior to expanding the stent.

40. A method for treating a vascular body lumen, comprising:

introducing a catheter sheath having a distal end and a compliant portion near the distal end and a radially expandable stent over the compliant portion into the body lumen and positioning the stent beyond an area of the lumen to be treated;

ultrasonically imaging the body lumen to obtain an image of the treatment area;

withdrawing the sheath to align the stent with the treatment area;

introducing a radially expandable member through the catheter sheath and up to the stent; and radially expanding the expandable member within the compliant portion to radially expand the stent within the body lumen at the treatment area.

* * * * *

UNITED STATES PATENT AND TRADEMARK OFFICE
CERTIFICATE OF CORRECTION

PATENT NO. : 5,707,354
DATED : January 13, 1998
INVENTOR(S) : Salmon et al.

It is certified that error appears in the above-identified patent and that said Letters Patent is hereby corrected as shown below:

Column 5, line 35, change "complaint" to --compliant--.

Column 7, line 31, change "complaint" to --compliant--.

Column 10, line 15, change "and" to --an--.

Column 10, line 51, change "complaint" to --compliant--.

Column 11, line 17, change "complaint" to --compliant--.

Column 10, line 54, change "lumen wherein" to --lumen,wherein--.

Signed and Sealed this

Twenty-seventh Day of July, 1999

Attest:

Q. TODD DICKINSON

*Attesting Officer*  *Acting Commissioner of Patents and Trademarks*